United States Patent [19]

van Beek et al.

[11] Patent Number: 5,990,253

[45] Date of Patent: *Nov. 23, 1999

[54] INDENYL COMPOUNDS AND CATALYST COMPONENTS FOR THE POLYMERIZATION OF OLEFINS

[75] Inventors: Johannus A. M. van Beek; Johannes G. de Vries, both of Maastricht; Henricus J. Arts, Sittard; Radjindrakumar Persad, Wessem; Gerardus H. J. van Doremaele, Sittard, all of Netherlands

[73] Assignee: DSM N.V., Heerlen, Netherlands

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/812,675

[22] Filed: Mar. 10, 1997

Related U.S. Application Data

[62] Division of application No. 08/439,449, May 11, 1995, Pat. No. 5,646,322, which is a continuation of application No. PCT/NL93/00229, Nov. 3, 1993.

[30] Foreign Application Priority Data

Nov. 11, 1992 [NL] Netherlands ............................ 9201970

[51] Int. Cl.$^6$ ...................................................... C08F 4/64
[52] U.S. Cl. ........................... 526/127; 526/160; 526/943; 526/352; 502/155; 556/11; 556/15; 556/43; 556/53
[58] Field of Search .................................. 526/127, 160, 526/943

[56] References Cited

U.S. PATENT DOCUMENTS

| | | |
|---|---|---|
| 4,078,131 | 3/1978 | de Zarauz . |
| 4,769,428 | 9/1988 | Zboril ........................................ 526/84 |
| 5,001,205 | 3/1991 | Hoel . |
| 5,017,714 | 5/1991 | Welborn, Jr. ............................... 556/12 |
| 5,071,808 | 12/1991 | Antberg ................................. 502/107 |
| 5,120,867 | 6/1992 | Welborn, Jr. ............................... 556/12 |
| 5,145,819 | 9/1992 | Winter .................................... 502/117 |
| 5,191,042 | 3/1993 | Cozewith . |
| 5,268,495 | 12/1993 | Riepl et al. ............................... 556/11 |
| 5,276,208 | 1/1994 | Winter ...................................... 556/53 |
| 5,350,817 | 9/1994 | Winter et al. . |
| 5,372,980 | 12/1994 | Davis . |
| 5,391,789 | 2/1995 | Rohrmann ................................. 556/11 |
| 5,455,365 | 10/1995 | Winter et al. . |
| 5,543,373 | 8/1996 | Winter et al. . |
| 5,576,260 | 11/1996 | Winter et al. . |
| 5,646,322 | 7/1997 | van Beek et al. . |

FOREIGN PATENT DOCUMENTS

| | | |
|---|---|---|
| 1-277004 | 8/1988 | European Pat. Off. . |
| 1-287666 | 10/1988 | European Pat. Off. . |
| 0 347 128 A1 | 12/1989 | European Pat. Off. . |
| 2-344887 | 12/1989 | European Pat. Off. . |
| 2-360492 | 3/1990 | European Pat. Off. . |
| 2-372414 | 6/1990 | European Pat. Off. . |
| 1-420436 | 4/1991 | European Pat. Off. . |
| 2-427339 | 5/1991 | European Pat. Off. . |
| 2-427697 | 5/1991 | European Pat. Off. . |
| 1-485821 | 5/1992 | European Pat. Off. . |
| 1-485823 | 5/1992 | European Pat. Off. . |
| 1-500944 | 9/1992 | European Pat. Off. . |
| 0 545 140 A1 | 6/1993 | European Pat. Off. . |
| WO-91/02012 | 2/1991 | WIPO . |
| WO-91/09882 | 7/1991 | WIPO . |

OTHER PUBLICATIONS

HH Brintzinger et al. (1995) Angew. Chem. Int. Ed. Engl, 34, 1143 (pp. 1143–1145 & ref).

Whelan, T., "Polymer Technology Dictionary," Chapman & Hall, London, 1994, entry under "x–olefin" at p. 1.

*Primary Examiner*—David W. Wu
*Attorney, Agent, or Firm*—Pillsbury Madison & Sutro LLP

[57] ABSTRACT

The invention relates to an indenyl compound of the general formula $$R'Ind\text{—}M\text{—}(Cp)Q_k$$

in which the symbols have the following meanings:

Ind: an indenyl group

R': a substituent, other than hydrogen, to the Ind group,

Cp: a cyclopentadienyl group

M: a transition metal from group 3, 4, 5 or 6 of the Periodic System of Elements Q: a ligand to M and k is an integer linked to the valence of M.

The invention is characterized in that the R' group is bound to the Ind group at the 2-position. The indenyl compound is a catalyst component for the polymerization of olefins. The invention also relates to polymers obtainable with such indenyl compounds.

18 Claims, No Drawings

INDENYL COMPOUNDS AND CATALYST COMPONENTS FOR THE POLYMERIZATION OF OLEFINS

RELATED APPLICATIONS

This is a divisional application of U.S. application Ser. No. 08/439,449 filed May 11, 1995 now U.S. Pat. No. 5,646,322 which is a continuation of PCT/NL93/00229 filed Nov. 3, 1993.

FIELD OF THE INVENTION

The invention relates to indenyl compounds that can be used as catalyst component for the polymerisation of olefins. The invention also relates to a process for the polymerisation of olefins and to a polyolefin.

Indenyl compounds are known as catalyst component for olefin polymerisation. The catalysts obtained using indenyl compounds exhibit a high polymerisation activity. See for example DE-A-3,840,772. The known indenyl compounds have the general formula:

$$R'Ind-M-(Cp)Q_k \qquad (1)$$

in which the symbols have the following meanings:
 Ind an indenyl group,
 R' a substituent, other than hydrogen, to the Ind group,
 Cp a cyclopentadienyl group,
 M a transition metal from group 3, 4, 5 or 6 of the Periodic System of Elements,
 Q a ligand to M.

The Periodic System of Elements is understood to be the new IUPAC version as printed on the inside cover of the Handbook of Chemistry and Physics, 70th edition, CRC Press, 1989-1990.

In formula (1), k is an integer linked to the valence of M in the following manner: k equals the valence of M minus two divided by the valence of the Q group. The Ind group and the Cp group are both bound to the metal M.

SUMMARY AND OBJECTS OF THE INVENTION

The said compounds are regarded as belonging to the metallocene compounds (metallocenes).

One of the aims of the invention is to provide new indenyl compounds with the general formula (1). Another aim is to provide an indenyl compound having favourable properties as a catalyst component in olefin polymerisation.

The invention concerns an indenyl compound having the general formula (1), characterized in that the substituent R' in formula (1) is bound to the Ind group at the 2-position. Here and hereinafter such a compound will be referred to as 2-indenyl compound (2-Ind). In the known indenyl compounds the substituent R' is bound to the 1-position of the indenyl ring; the known indenyl compounds are therefore 1-indenyl compounds.

DETAILED DESCRIPTION OF THE INVENTION

In general and in this description, the substituent locants of the indenyl ring are numbered in accordance with the IUPAC Nomenclature of Organic Chemistry, 1979, rule A 21.1. The numbering of the substituent locants for indene is given below. This numbering is analogous in the case of an Indenyl ring:

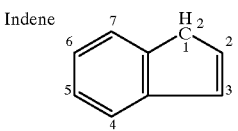

According to the invention 2-indenyl compounds were found to exhibit an activity different from that of the known 1-indenyl compounds in olefin polymerisation. In the solution polymerisation of olefins, in particular in the polymerisation to polyethylene, such compounds exhibit higher activity. In the production of ethylene-α-alkene-(third monomer) rubbers (the so-called EA(D)M rubbers) they lead to products that differ from the usual products obtained with metallocenes, among other things to products with a very low content of crystalline material.

In the compounds according to the invention the Cp group in formula (1) is a cyclopentadienyl group or a derivative thereof, like for example a fluorenyl group or an indenyl group, all of them whether or not substituted.

From EP-A-485,821 and EP-A-485,823 bisindenyl-metallocenes are known having a bridge coupled to the 1-positions of the indenylgroups. Such metallocenes are expressly excluded.

In EP-A-500,944 an halogenated metallocene, bis(2,3-dimethyl-1-indenyl)zirconiumdichloride is mentioned. This metallocene is also expressly excluded from the 2-indenyl compounds of the invention.

EP-A-372,414 indicates two specific halogenated, bridged metallocenes. The chemical names of the two metallocenes (of formula II-1 and II-2 on page 5 of said EP-A) are:
 ethylene-1-(3-but-3-enyl)inden-1-yl)-2-((1-but-3-enyl)-inden-2-yl)zirconiumdichloride, and
 ethylene-1-((3-allyldimethylsilyl)-inden-1-yl)-2-((1-allyldimethylsilyl)-inden-2-yl)zirconiumdichloride.

Also these two bisindenyl compounds are expressly excluded from the 2-indenyls of the invention.

The above mentioned disclaimers relative to the prior art are justified as neither in the texts nor in examples thereof it is disclosed or suggested that these metallocenes, in which the above indicated Cp-group is an indenylgroup, form part of the generic group of 2-indenyl-metallocenes, having the properties as described hereinabove.

Besides that the R' group is present in the indenyl compound at the 2-position, the indenyl group (the Ind group in formula 1) may optionally also be substituted at other positions. The Cp group may also be substituted. As R' group, a hydrocarbon group (like alkyl, aralkyl, aryl) or a group with at least one heteroatom from group 14, 15 or 16 of the Periodic System of Elements may be used. Examples of such a heteroatom containing group are: alkylsulphides (like MeS-, PhS-, n-butyl-S-), amines (like $Me_2N$-, n-butyl-N-), Si or B containing groups (like $Me_3Si$- or $Et_2B$-) or P-containing groups (like $Me_2P$- or $Ph_2P$-). Hydrogenated forms of 2-indenyl compounds also fall within the spirit of the invention.

As a substituent at a position other than the 2-position of the Ind group or the Cp group such groups as indicated above for R' may also be used.

According to the invention, when R' is a hydrocarbon group, R' is preferably an alkyl group, more in particular an alkyl group with 1–4 carbon atoms.

The Q group in the compounds according to the invention comprises one or more uni- or polyvalent anionic ligands to the transition metal. As examples of such ligands, which may be the same or different, the following can be mentioned:

a hydrogen atom, a halogen atom, an alkyl group, an aryl group, an aralkyl group, an alkoxy group, an aryloxy group, a group with a heteroatom chosen from group 14, 15 or 16 of the Periodic System of Elements, such as an amine group or amide group, an S compound, such as sulphide, sulphite, sulphate, thiol, sulphinate, a P compound, such as phosphine, phosphite, phosphate.

The skilled in the art can determine the suitability of these and other ligands through simple experimenting. The number of Q groups in the 2-indenyl compound according to the invention (index k in formula (1)) is determined by the valence of the transition metal M and the valence of the Q groups itself.

The transition metal in the 2-indenyl compound (the M group) is chosen from groups 3 through 6 of the Periodic System of Elements. The transition metal is preferably chosen from the group Ti, Zr, Hf, V, Nb, Cr, Ta, Sm and Mo. Zr, Hf or Ti are greatly preferred.

Another preferred embodiment of the invention is formed by compounds in which the Cp group is a 2-indenyl group with the formula:

R"Ind  (3)

where R" is a substituent other than hydrogen at the 2-position of the Ind group. As R" group, a hydrocarbon group (like alkyl, aryl, aralkyl) or a group with at least one heteroatom from group 14, 15 or 16 of the Periodic System of Elements may be used. Such a substituent can be the same as or different from the substituent used as R'. The R" group, when being a hydrocarbon group, is preferably an alkyl group, in particular an alkyl group with 1–4 carbon atoms. When used as, for example, catalyst in the solution polymerisation of ethylene at reaction temperatures of at least 130° C. these compounds have a high catalytic activity, and in the production of ethylene-α-alkene-(third monomer) rubbers they lead to products with a very low content of crystalline material.

In another preferred embodiment of the invention, the indenyl group of formula (1) is a group in which is R' is linked to the Cp group in formula (1). These compounds, in which R1 forms a bridge between the 2-position of the Ind group and the Cp group in formula (1), are referred to as bridged 2-indenyl compounds according to the invention. The other compounds according to formula (1), without the bridge between the 2-indenyl group and the Cp group, are referred to as unbridged 2-indenyl compounds. In particular, in a bridged 2-indenyl compound the Cp group in formula (1) is a 2-indenyl group as well, which is bound to the R' group at the 2-position. Such compounds according to the invention are referred to as bridged bis(2-indenyl) compounds; in such a case the R' group forms a bridge between two 2-indenyl groups, hence the term bridged bis(2-indenyl) compound. The formula of these bridged bis(2-indenyl) compounds according to the invention may be represented as follows:

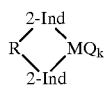

(4)

where

R is a group derived from R'.

In a bridged bis(2-indenyl) compound according to the invention, R can be a hydrocarbon group (like an alkenyl group, an arylalkenyl group) or a group with at least one heteroatom from group 14, 15 or 16 of the Periodic System of Elements. Preferably the choice of the R group, when being a hydrocarbon group, is between a methylidene group and an ethylidene group. If R contains a heteroatom, this heteroatom is preferably chosen from the group comprising silicon, nitrogen, phosphorus, oxygen or sulphur. Examples from R-groups containing a heteroatom are: sulphur or —(CH$_2$)$_2$—S—(CH$_2$)$_2$—, oxygen, Me$_2$Si=, —SiMe$_2$—SiMe$_2$—, (CH$_3$)$_2$GE=, PhP= or PhN=. The hydrocarbon groups in these R-groups containing a heteroatom may be varied and can be an alkyl, aryl or aralkylgroup. With such bridged bis(2-indenyl) compounds as catalyst component, good results are obtained in the solution polymerisation of ethylene and in the synthesis of EA(D)M rubbers.

The 2-indenyl compounds according to the invention can be prepared via different synthesis routes, consisting of synthesis steps known as such. They can for example be prepared by converting a 2-indene compound into its anion. Compounds that are suitable for converting the 2-indene compound into the anion are organometallic compounds, amines, metal hydrides and alkaline or alkaline earth metals. Organolithium, organomagnesium and organosodium compounds can for example be used for this purpose, but also sodium or calcium. In particular organolithium compounds are highly suitable, preferably methyl-lithium or n-butyl-lithium.

The elucidation of the further synthesis steps will be based on the use of a lithium anion, but the invention is by no means limited to this. In the case of non-bridged ligands the conversion takes place via reaction with 1 equivalent organolithium compound to obtain the mono-anion, and in the case of bridged ligands via reaction with 2 equivalents organolithium compound to obtain the di-anion.

The 2-indenyl anion thus prepared is subsequently converted into the 2-indenyl compound of the invention by trans-metalation with a compound of a transition metal from groups 3, 4, 5 or 6 of the Periodic System of Elements (M in formula (1)). See for example EP-A-420,436, EP-A-427,697. The process described in NL-A-91,011,502 is particularly suitable. Examples of transition metal compounds that are suitable for trans-metalation are TiCl$_4$, ZrCl$_4$, HfCl$_4$, Zr(OBu)$_4$ and Zr(OBu)$_2$Cl$_2$. The trans-metalation is preferably carried out as in NL-A-91,011,502, in a solvent or in a combination of solvents that weakly coordinate to transition metals from the groups 3, 4, 5 or 6 with at most 1 mole equivalent, relative to the transition metal compound started from, of a Lewis base of which the conjugated acid has a pK$_a$ greater than −2.5. Examples of suitable solvents/dispersants (pK$_a$ of conjugated acid ≦−2.5) are ethoxyethane, dimethoxyethane, isopropoxyisopropane, n-propoxy-n-propane, methoxybenzene, methoxymethane, n-butoxy-n-butane, ethoxy-n-butane and dioxane. Part of the reaction medium may consist of hydrocarbons (hexane and the like). In the said trans-metalation LiCl is formed besides the metallocene. This usually precipitates in the dispersants used. If the metallocene precipitates too, the combination of metallocene and LiCl as such can be used with a co-catalyst (aluminium compound or cation-generating agent) for the polymerisation of olefins. The LiCl may also be separated from the metallocene, for example by dissolving the metallocene in dichloromethane and filtering LiCl off. If the metallocene dissolves in the solvent used in the synthesis, the LiCl can be separated at once by filtration.

The 2-indene compounds mentioned heretofore as compounds started from can be formed from commercially available compounds, via synthesis routes consisting of several known reaction steps. The synthesis route is chosen on the basis of the 2-indenyl compound desired. The unbridged 2-indenyl compounds, for example, can be prepared from 2-indanones, which are commercially available, via reaction with an alkyl magnesium halide, followed by dehydration. The synthesis of the bridged 2-indenyl compounds strongly depends on the 2-indenyl compound desired. Various synthesis routes are described in the examples given hereafter.

The 2-indenyl compounds according to the invention can be used, via methods known for metallocenes, as catalyst component for the polymerisation of one or more olefins. Particularly the olefin(s) is/are chosen from the group comprising α-olefins, internal olefins and diolefins. Mixtures of these can also be used.

The invention relates in particular to a process for the polymerisation of (an) α-olefin(s). The olefin or α-olefin(s) is/are preferably chosen from the group comprising ethylene, propylene, butene, pentene, heptene and octene, while mixtures can also be used. More preferably, ethylene and/or propylene is/are used as the olefin. The use of such olefins leads to the formation of crystalline polyethylene homopolymers and copolymers of both low and high density (HDPE, LDPE, LLDPE, etc.), and polypropylene homopolymers and copolymers (PP and EMPP). The monomers needed fur such products and the processes to be used are known to the skilled in the art.

The process according to the invention is also eminently suitable for the preparation of amorphous or rubbery copolymers based on ethylene and another α-olefin. Propylene is preferably used as the other α-olefin, so that EPM rubber is formed. It is also quite possible to use a diene besides ethylene and the other α-olefin, so that a so-called EADM rubber is formed, in particular EPDM (ethylene propylene diene rubber).

The 2-indenyl compounds according to the invention can be used as catalyst, both supported and unsupported. The supported catalysts are mainly used in gas-phase and slurry processes. The support is any support known as support for metallocene catalysts, for example $SiO_2$ or $Al_2O_3$.

The 2-indenyl compounds according to the invention are particularly suitable for an unsupported catalyst in solution polymerisation processes. In solution polymerisation the known solvents may be used. Preferably aliphatic hydrocarbons, such as hexane and heptane, and mixtures of aliphatic hydrocarbons are used.

If an aliphatic hydrocarbon is used as solvent, the solvent may still contain small amounts of aromatic hydrocarbon, for example toluene. If methylaluminoxane (MAO) is used as co-catalyst, for example, toluene may serve as solvent to make it possible to meter the MAO to the polymerisation reactor in solution.

In the solution polymerisation of either ethylene or ethylene with other α-olefins and/or non-conjugated dienes at comonomer contents of up to 25%, reactor temperatures of at least 130° C. are used, in order to keep the polymer produced in solution. At weight percentages of incorporated comonomer of from 30 to 80% the catalysts according to the invention yield such homogeneous products that the polymerisation can be carried out at much lower reactor temperatures ($\geq 30°$ C.) without the polymer formed precipitating from the solution. Suitable other α-olefins are for example propylene, butene, hexene and octene.

Polymerisation of the olefin can take place in a known manner, in the gas phase as well as in a liquid reaction medium. In the latter case both solution polymerisation and suspension polymerisation are options.

The process according to the invention will hereafter be elucidated with reference to the EP(D)M preparation known per se, which is representative of the olefin polymerisations meant here. For the preparation of other polymers based on an olefin the reader is emphatically referred to the multitude of publications on this subject.

As suitable α-olefins that may be used as monomer besides ethylene in the preparation of an EA(D)M polymer, the following may be mentioned: propylene, butene-1, pentene-1, hexene-1, octene-1 or the branched isomers thereof, for example 4-methylpentene-1, and in addition styrene, α-methylstyrene. Mixtures of these alkenes may also be used, propylene and/or butene-1 being preferred.

As diene to be used in such an amorphous copolymer a polyunsaturated compound is started from, which may be used and serves to incorporate unsaturation in the polymer; it contains at least two C=C bonds and may be aliphatic or alicyclic. Aliphatic polyunsaturated compounds generally contain from 3 to 20 carbon atoms, the double bonds being conjugated or, preferably, unconjugated. Examples hereof are: 1,3-butadiene, isoprene, 2,3-dimethyl-1,3-butadiene, 2-ethyl-1,3-butadiene, piperylene, mycrene, allene, 1,2-butadiene, 1,4,9-decatrienes, 1,4-hexadiene, 1,5-hexadiene and 4-methyl-1,4-hexadiene.

Alicyclic polyunsaturated compounds, which may or may not contain a bridgeing group, may be either monocyclic or polycyclic. Examples of such compounds are norbornadiene and its alkyl derivatives; the alkylidene norbornenes, in particular the 5-alkylidene-2-norbornenes, in which the alkylidene group contains from 1 to 20, preferably from 1 to 8 carbon atoms; the alkenyl norbornenes, in particular the 5-alkenyl-2-norbornenes, the alkenyl group of which contains from 2 to 20, preferably from 2 to 10 carbon atoms, for example vinylnorbornene, 5-(2'-methyl-2'butenyl)-2-norbornene and 5-(3'-methyl-2 'butenyl)-2-norbornene; dicyclopentadiene and the polyunsaturated compounds of bicyclo-(2,2,1)-heptane, bicyclo-(2,2,2)-octane, bicyclo-(3, 2,1)-octane and bicyclo-(3,2,2)-nonane, at least one of the rings being unsaturated. Furthermore, compounds such as 4,7,8,9-tetrahydroindene and isopropylidenetetrahydroindene may be employed. Dicyclopentadiene, 5-methylene-2-norbornene or 5-ethylidene-2-norbornene or 1,4-hexadiene are used in particular. Mixtures of the aforementioned compounds may also be used.

The diene may be present in the copolymer in amounts of up to 30% (wt), preferably up to 10–15% (wt).

In addition to or in place of the diene, an unsaturated compound containing one or more functional groups such as halogen atoms, OH, OR, COOH, COOR or $NH_2$ groups may be incorporated in the copolymer if desired, in an amount of up to 20% (wt).

The molar ratio of the monomers applied is dependent on the desired polymer composition. Given the widely varying polymerisation rates of the monomers, it is not possible to give a universal range for the molar ratios. Normally, for the copolymerisation of ethylene and propylene a molar ratio of between 1:1 and 1:5 will be selected. If a polyunsaturated compound is to be copolymerised, the molar ratio thereof relative to ethylene will usually be from 0.0001:1 to 1:1.

The polymerisation reaction is usually effected at a temperature of between −40 and 200° C., preferably between 10 and 80° C. The pressure will usually be 0.1–5 Mpa but higher or lower operating pressures are also possible. The process is preferably conducted continuously but may also be conducted semi-continuously or batchwise.

The residence time may vary from a few seconds to a few hours. The residence time will normally be chosen to be between a few minutes and one hour.

The polymerisation may take place in a liquid which is inert with respect to the catalyst, e.g. in one or more saturated aliphatic hydrocarbons such as butane, pentane, hexane, heptane, pentamethylheptane or petroleum fractions; in aromatic hydrocarbons, e.g. benzene or toluene, or in halogenated aliphatic or aromatic hydrocarbons, e.g. tetrachloroethylene. The operating temperature and pressure may be so chosen that one or more of the applied monomers, particularly the α-olefin, e.g. propylene, is liquid and is present in so large an amount that it acts as a dispersant. In that case, another dispersant is not needed. The process according to the invention may be conducted in a gas-filled or a liquid-filled polymerisation reactor or in a completely liquid-filled reactor. The use of a heterogenized catalyst allows the polymerisation process to be effected in suspension or in the gas phase.

The molecular weight can be adjusted by techniques known to one skilled in the art. More particularly, this can be done by applying chain terminating agents such as diethyl zinc and preferably with hydrogen. Even very small amounts of hydrogen will suitably influence the molecular weight.

After polymerisation, the polymer may be worked up in various ways. For liquid-phase processes, this may be done by evaporating the solvent or by steam coagulation.

Amorphous copolymers obtained by the process according to the invention generally contain between 25 and 85% (wt) ethylene. However, products with an ethylene content of between 40 and 75% (wt) are preferred.

Such copolymers are suitable for a plurality of applications, e.g. the manufacture of hoses, conveyor belts, sealing profiles. If desired, they may be vulcanized by the usual methods (for instance with the aid of free-radical donors, such as peroxides, or with sulphur).

In order to allow the product to be processed as a rubber, the copolymer may be extended with oil; this is preferably done during the polymerisation process. It is known to add agents so as to prepare a friable bale. This may be effected by, for instance, adding talc or by employing a system as described in EP-A-427,339. The composition described therein, comprising an inorganic partioning agent, a thickener and binder reagent and an anionic dispersant, has been found to be well suited for use in the products according to the invention.

In the preparation of EP(D)M the metallocenes of the present invention exhibit great differences from the traditional V-based Ziegler catalysts (such as $VOCl_3$ and its derivatives). For example, the metallocene compound has a relatively high affinity to propylene and a much lower affinity to the third monomer. Also, propylene inversion takes place to a much lesser degree (approx. 20% in the case of the traditional catalyst and only approx. 0–5% if a metallocene according to the invention is used, measured with the aid of C13-NMR). Consequently, altogether different EP(D)M structures are obtained.

The 2-indenyl compounds are applied in known manner, whether or not in combination with a cocatalyst, which is usually an organometal compound, in which the metal is chosen from group 1, 2, 12 or 13 of the Periodic System of Elements. Preference is given to an aluminium compound. For aluminium compounds-based cocatalysts, reference can be given to for instance EP-A-287,666, pages 20-21. Also suitable as cocatalysts are benzene-insoluble organo-aluminium-oxy compounds as disclosed in EP-A-360,492. See also U.S. Pat. No. 4,769,428 (5th column), where organoaluminium alkyls and linear and cyclic aluminoxanes are used as cocatalysts. The aluminoxanes may be prepared in the manner disclosed in these patent publications; they are also commercially available. Examples of commercially available aluminoxanes include methylaluminoxanes as manufactured by Schering, Ethyl and Akzo.

The 2-indenyl compounds according to the invention may also be employed in the polymerisation of olefins without aluminoxanes being used as cocatalysts. The 2-indenyl compounds may, for instance, be converted to cationic compounds, which have catalytic activity. For the conversion into cationic compounds refer to, for instance, WO-A-91,09,882, EP-A-277,004 or WO-A-91,02,012.

The 2-indenyl compounds according to the invention, in solid form or when suspended in an inert solvent, are highly stable and can therefore be stored for prolonged periods of time.

The invention further relates to a polyolefin obtainable by polymerisation of (an) olefin(s) using a 2-indenyl compound according to the invention as a catalyst component. This particularly concerns EA(D)M polymers that stand out from state-of-the art products by a very small number of α-olefine inversions; the products according to the invention preferably have 0–5% α-olefine inversions in the chain.

The invention will be illustrated by the following examples and comparative experiments. The indenyl compounds that were synthesized were analyzed through neutron activation analysis and H-NMR (hydrogen nuclear magnetic resonance). Neutron activation analysis was used to determine, for instance, the transition metal and halogen contents. H-NMR resulted in informations about the structure of the indenyl compounds. The H-NMR analyses were conducted using a Bruker AC200 NMR instrument at a frequency of 200 MHz. The samples for NMR analysis were prepared by adding c. 1 ml of deuterobenzene to 1–10 mg of the indenyl compound.

The crystallization behaviour of the polymers obtained was determined by differential scanning calorimetry (DSC). After rapidly heating the sample to 200° C. and holding it at that temperature for 5 minutes, the sample is cooled to −70° C. at the rate of 10° C./minute. The accompanying thermal effects are recorded.

A "Hoekstra" value (a measure of the plasticity of the product) was measured on the rubbery polymers. This is done by placing a rubber sheet between two platens at a temperature of 106° C. The platens are positioned at a distance of 1 mm. A load of 10 $kg/cm^2$ is applied after 30 seconds so as to measure the distance between the platens after 15 seconds. The percentage decrease in thickness is the value of the Hoekstra plasticity.

The intrinsic viscosity of the polymers obtained was determined by dissolving in decalin at 130° C.

EXAMPLES

Examples I–III and comparative experiments A–C describe the synthesis of unbridged indenyl compounds. Examples IV–IX and comparative experiments D–C con-

9 cern the application of these unbridged indenyl compounds as catalysts for the polymerisation of (an) olefin(s).

Examples X–XIV describe the synthesis of bridged 2-indenyl compounds whilst examples XV–XIX concern the polymerisation of (an) olefin(s) with these compounds.

Examples XX–XXIII describe the synthesis of unbridged 2-indenyl compounds having a hetero atom containing group as substituent on the 2-position of the indenyl, whilst examples XXIV–XXVII describe the polymerisation of an olefin with these compounds.

Example I

I.1. Synthesis of 2-methylindene 50 ml of diethylether was added to 2.5 grams of magnesium. A solution of 14.3 grams of methyliodide in 50 ml of diethylether was added for 1 hour while cooling with a water bath. The reaction mixture was then stirred at room temperature for 30 minutes. To this reaction mixture was added a solution of 13.2 grams of 2-indanone in 40 ml of diethylether, whereupon the mixture was stirred for 30 minutes. Hereafter, 100 ml of water was added. The organic layer was separated from the water layer. This water layer was washed twice with 50 ml of dichloromethane, whereafter the combined organic layers were dried on magnesium sulphate. On filtering off the drying agent, the filtrate was evaporated, leaving 14.0 grams of residue. This residue was dissolved in 100 ml of toluene, 4 drops of concentrated sulphuric acid were added and the resulting reaction mixture was refluxed for 30 minutes. After cooling down to room temperature, the mixture was washed once with 50 ml of water. The toluene was evaporated and the residue was vacuum distilled. Yield: 4.0 grams of 2-methylindene (30%).

I.2. Synthesis of bis(2-methylindenyl) zirconium dichloride 17.9 ml of n-butyllithium (n-BuLi) (1.6 M solution in hexane) was added to a solution of 3.72 grams of 2-methylindene in 40 ml of diethylether at −56° C. On removal of the coolant the reaction mixture was stirred for 2 hours (room temperature was reached after 30 minutes). The reaction mixture was then cooled to −56° C. and combined with a suspension of 3.33 grams of zirconium tetrachloride in 40 ml of diethylether (also previously cooled to −56° C.). The coolant was removed and the reaction mixture was stirred for 2 hours (reaction toke place within a few seconds). Hereafter, the solid (bis(2-methylindenyl) zirconium dichloride with complexed lithium chloride) was filtered off. The residue obtained was washed once with 25 ml of diethylether and twice with 50 ml of gasoline (which is a mixture of aliphatic hydrocarbons with a boiling range from 65–70° C.) and then vacuum dried for some hours. Yield: 5.27 grams of a yellow solid, bis(2-methylindenyl) zirconium dichloride.

Example 2

II.1. Synthesis of 2-ethylindene

The same synthesis route was followed as in example I.1 except that ethyl magnesium bromide (70 ml 3.0 M in diethylether) and 13.4 grams of 2-indanone in 75 ml diethylether were used. The excess Grignard compound was neutralized with hydrochloric acid. This time the second step was effected with oxalic acid (15.2 grams) and 200 ml of water in two hours and with refluxing for a quarter. After this step the product was extracted with diethylether (3 times 50 ml). After the solvent had been evaporated, purification took place through a silica column (mobile phase 40–60 petroleum ether). Yield: 4.5 grams of 2-ethylindene (31%).

II.2. Synthesis of bis(2-ethlindenyl)zirconium dichloride

As in example I.2 except with:

2.45 grams of 2-ethylindene 10.2 ml of n-BuLi 2.00 grams of zirconium tetrachloride.

Obtained was 2.6 grams of a yellow solid: bis(2-ethylindenyl) zirconium dichloride.

Example III

III.1. Synthesis of 2-butylindene

Procedure as in example I.1 except with: 2.4 grams of magnesium, 14.0 grams of 1-bromobutane, 13.3 grams of 2-indanone, solvent diethylether. Water and hydrochloric acid were added after reaction. The organic layer was separated from the water layer, which was washed three times with diethylether, and the combined organic layers were evaporated, the residue being mixed with toluene (150 ml). The mixture was refluxed with concentrated sulphuric acid (4 drops). After reacting, the mixture was washed with water (two times 50 ml), evaporated and purified through a silica column. Yield: 7.0 grams of 2-butylindene (41%).

III.2. Synthesis of bis(2-butylindenyl) zirconium dichloride

As in example I.2 except with:

3.74 grams of 2-butylindene 13.6 ml of n-BuLi 2.53 grams of zirconium tetrachloride.

The product was dissolved in diethylether and passed through a glass filter (for removal of lithium chloride). After evaporating the filtrate, 3.31 grams of a solid compound, bis(2-butylindenyl) zirconium dichloride, was obtained.

Comparative experiment A

A.1. Synthesis of 1-methylindene

Indene was reacted with BuLi to form indenyl lithium, which compound was reacted with methyl iodide to form 1-methylindene. Use was made of: 18.2 grams of indene, 100 ml of n-BuLi solution, 22.0 grams of methyl iodide.

Yield: 13.2 grams of 1-methylindene (65%).

A.2. Synthesis of bis(1-methyl-indenyl) zirconium dichloride

As in Example I.2, but this time with:

3.98 grams of 1-methylindene, 18.3 ml of n-BuLi, 3.59 grams of zirconium tetrachloride.

4.20 grams of a solid yellow compound, bis(1-methyl-indenyl) zirconium dichloride, was obtained.

Comparative Experiment B

B.1. Synthesis of 1-ethylindene

As in comparative experiment A.1, but this time with:

17.6 grams of indene, 100 ml of n-BuLi solution, 23.6 grams of ethyl iodide.

Yield: 15.2 grams of 1-ethylindene (70%).

B.2. Synthesis of bis(1-ethylindenyl) zirconium dichloride

As in Example I.2, but this time with:

4.04 grams of 1-ethylindene, 17.5 ml of n-BuLi, 3.25 grams of zirconium tetrachloride. p 5.20 grams of a solid yellow compound, bis(1-ethyl-indenyl) zirconium dichloride, was obtained.

Comparative Experiment C

C.1. Synthesis of 1-butylindene

As comparative experiment A.1, but this time with lithium diisopropylamide prepared in situ. The following ingredients were used:

15 ml of diisopropylamine, 60 ml of BuLi solution, 11.9 grams of indene, 13.8 grams of butylbromide.

Yield: 5.1 grams of 1-butylindene (29%).

C.2. Synthesis of bis(1-butylindenyl) zirconium dichloride

As in Example III.2, except with:

2.98 grams of 1-butylindene, 10.8 ml of n-BuLi, 2.02 grams of zirconium tetrachloride.

4.16 grams of a solid yellow compound, bis(1-butylindenyl) zirconium dichloride, was obtained.

Example IV
Ethylene Polymerisation 425 ml of pentamethylheptane (isododecane, abbreviation PMH) and ethylene were dosed to a 1.3-liter reactor, while the reactor was being heated until a temperature of 140° C. was reached. Next, 25 ml of a methylaluminoxane (MAO) solution in toluene (Schering, 1.6 M) was added. At a temperature of 155° C. 3 ml of a 0.015 M solution of the catalyst of Example III in hexane was added, followed by an after-rinse with 50 ml of PMH. The total system pressure was 2 MPa and was kept constant by adding ethylene. As a result of the reaction (polymerisation), the temperature rose to 200° C. After 20 minutes the polymerisation was stopped and the polyethylene was isolated and dried. Yield: 72 grams of polyethylene (PE).

Example V
Ethylene Polymerisation

Polymerisation as in Example IV, except with: 15 ml of an MAO/toluene solution (Schering, 1.6 M), 5 ml of a 0.015 M solution of the catalyst of Example III in hexane.

As a result of the reaction (polymerisation), the temperature rose to 191° C. After 20 minutes the polymerisation was stopped and the polyethylene was isolated and dried. Yield: 111 grams of polyethylene (PE).

Example VI
Ethylene/Propylene Polymerisation

The reaction product of Example I was used for solution copolymerisation of ethylene and propylene. Reaction product 1 in spirit (slurry) and MMAO® (Akzo, modified MAO 3A) in heptane were added to a 1.5-liter reactor filled with 450 ml of gasoline, at a feed temperature of 30° C. and a pressure of 0,7 MPa. An after-rinse was performed with 50 ml of gasoline. The propylene/ethylene ratio in the gas phase was 2. The zirconium concentration in the reactor was 4 $\mu$mol/l, the Al/Zr ratio was 1000. After 30 minutes' polymerisation at a maximum polymerisation temperature of 37° C., 10 grams of clear rubber (Hoekstra: 80), without visible homopolymer by-product, was isolated and worked up. The $C_3$ content was 48 wt. % and the DSC measurement revealed a crystallization peak at −28° C.

Example VII
Ethylene/Propylene Polymerisation

The reaction product of Example I was used for solution polymerisation of ethylene and propylene as described in Example VI. This time the Al/Zr ratio was 2500. After 30 minutes' polymerisation, during which the maximum polymerisation temperature was 41° C., 16 grams of clear rubber (Hoekstra: 45) without visible homopolymer by-product was isolated and worked up. The $C_3$ content was 52 wt. % and the DSC measurement revealed no crystallization peak above −50° C.

Example VIII
Ethylene/Propylene Polymerisation

The reaction product of Example II was used for solution copolymerisation of ethylene and propylene as described in Example VI. The Al/Zr ratio was 2500. After 30 minutes' polymerisation, during which the maximum polymerisation temperature was 38° C., 10 grams of clear rubber (Hoekstra: 72) without visible homopolymer by-product was drained and worked up. The $C_3$ content was 51 wt. %; the DSC measurement revealed no crystallization peak above −50° C.

Example IX
Ethylene/Propylene Polymerisation

The reaction product of Example II was used for solution polymerisation of ethylene and propylene as described in Example VI. The Al/Zr ratio was now 1000. After 30 minutes' polymerisation, during which the maximum polymerisation temperature was 36° C., 8.5 grams of clear rubber (Hoekstra: 78) without visible homopolymer by-product was drained and worked up. The $C_3$ content was 53 wt. %; the DSC measurement revealed no crystallization peak above −50° C.

The products of examples VI–IX had <2% $C_3$ inversions in the chain.

Comparative Experiment D
Ethylene Polymerisation

Polymerisation took place as described in Example IV, except that the catalyst of Comparative Experiment C was used. The following ingredients were dosed:

2.5 ml of a 0.015 M solution of the catalyst in hexane, 15 ml of MAO (1.6 M, Schering).

Yield: 25 grams of polyethylene.

Comparative Experiment E
Ethylene Polymerisation

Polymerisation took place as described in Example IV, except that the catalyst of Comparative Eperiment C was used. In addition, MAO and catalyst were premixed for 1 minute and were dosed at an initial temperature of 155° C. The following ingredients were used:

1 ml of a 0.015 M solution of the catalyst in hexane, 10 ml of MAO (1.6 M, Schering).

Yield: 15 grams of polyethylene.

Comparative Experiment F
Ethylene/Propylene Polymerisation

Polymerisation as described in Example VI, but this time with the catalyst of Comparative Experiment A and with an Al/Zr ratio of 2500. The product yield was about 20 grams, but the stirrer and the walls were greatly fouled with deposits (mainly polyethylene).

Comparative Experiment G
Ethylene/Propylene Polymerisation

Polymerisation as described in Example VI, this time with the catalyst of Comparative Experiment B and with an Al/Zr ratio of 2500. The product yield was about 20 grams, but the product was inhomogeneous and the stirrer and the walls were fouled (mainly with polyethylene).

Example X
X.1. Synthesis of indenebromohydrin

At a temperature of about 4° C., 7.5 ml of water and 20.3 grams of N-bromosuccinimide were added to 11.6 grams of indene dissolved in 100 ml of dimethylsulphoxide (DMSO). The reaction mixture was stirred for 20 minutes and then poured out into 400 ml of saturated sodium bicarbonate solution. The precipitate was filtered off and washed with 100 ml of water. After recrystallization from a solution in chloroform/hexane the yield was 15.5 grams of indenebromohydrin (73%).

X.2. Synthesis of 2-bromoindene

To 14.3 grams of indenebromohydrin, dissolved in 150 ml of toluene, 0.5 ml of concentrated sulphuric acid was added, followed by stirring for 1 hour with refluxing, the water released being azeotropically separated. After cooling to room temperature, washing with water (two times 50 ml) and evaporation of toluene, the product was vacuum-distilled. Yield: 4.5 grams (43%) of pale yellow/green coloured 2-bromoindene.

X.3. Synthesis of dimethylbis(2-indene)silane

Starting from 4.3 grams of 2-bromoindene, the corresponding Grignard reagent was prepared, which was then added to a solution of 1.2 gram of dichlorodimethylsilane in 40 ml of tetrahydrofuran (THF). The dosing temperature was 45° C. and the dosing time 1 hour. Afterwards, the mixture was stirred for another 3 hours at 45° C. The product was worked up by successively adding water, evaporating THF, adding diethylether to the residue, washing the organic layer with water, drying this organic layer over magnesium sulphate, evaporating ether and purifying the residue over a silica column (mobile phase: hexane). Yield: 0.43 gram (13.7%) of a viscous, colourless liquid, dimethylbis(2-indene)silane.

X.4. Synthesis of (dimethylbis(2-indenyl)silane) zirconium dichloride

As in Example I.2, this time with:

0.71 gram of dimethylbis(2-indene)silane, 3.35 ml of n-BuLi, 0.62 gram of zirconium tetrachloride.

1.15 gram of a solid yellow compound (the compound of the title plus lithium chloride) was obtained.

Example XI

XI.1. Synthesis of thio(bis(2-indene))

2-Indanone (3.0 g) and Lawesson reagent (see S. Scheibye, R. Shabana and S.-O Lawesson, Tetrahedron 38, (1982), 993) (5.45 g) were heated for 2.5 hours in 40 ml of toluene with refluxing. Next, the reaction mixture was stirred for 12 hours at room temperature, after which the toluene was evaporated. The reaction product was purified with the aid of chromatography. The thio(bis-(2-indene)) yield was 21 g.

XI.2. Synthesis of (thio(bis(2-indenyl))) zirconium dichloride

As in Example I.2, this time with:

2.54 grams of thio(bis(2-indene)), 12.1 ml of n-BuLi, 2.72 grams of zirconium tetrachloride.

4.54 grams of a solid yellow compound, (thio(bis(2-indenyl))) zirconium dichloride, was obtained.

Example XII

XII.1. Synthesis of thio(bis(1-benzyl-2-indene))

15.0 grams of sodium carbonate was added to a solution of 13.6 grams of 2-indanone in 100 ml of THF. Next, a solution of 10.0 grams of pyrrolidine in 40 ml of THF was added to this mixture in 35 minutes, after which the mixture was stirred for 1 hour at room temperature. Working up of this reaction mixture yielded 18.7 grams (100%) of the corresponding enamine.

Of this enamine, 0.1 mol was refluxed for 7 hours with 19.4 grams of benzylbromide in 150 ml of acetonitrile. After evaporation of the solvent, water (100 ml), acetic acid (25 ml) and 100 ml of dichloromethane were added; the entire mixture was stirred for 18 hours. Working up of the organic layer yielded a product which was purified by vacuum distillation. Yield: 5.2 grams (23%).

The so obtained 1-benzyl-2-indanone was now reacted with Lawesson's reagent as described in Example XI.1, and after refluxing the mixture was stirred at room temperature for 20 hours. After evaporation of the toluene the product was boiled five times with 200 ml of hexane, after which the hexane layers were combined and the hexane was evaporated. Recrystallization from methanol yielded 2.5 grams (35%) of thio(bis(1-benzyl-2-indene)) as product.

XII.2. Synthesis of (thio(bis(1-benzyl-2-indenyl))) zirconium dichloride

As in Example I.2, this time with:

1.21 grams of thio(bis(1-benzyl-2-indene)), 3.4 ml of n-BuLi, 0.64 gram of zirconium tetrachloride.

1.11 gram of a solid yellow compound, (thio(bis(1-benzyl-2-indenyl))) zirconium dichloride, was obtained.

Example XIII

XIII.1. Synthesis of ethyl(2-indene)acetate

A solution of 31.3 grams of triethyl-phosphonoacetate in 75 ml of THF was dosed to a suspension of 3.30 grams of sodium hydride in 200 ml of THF, at 15° C., in five quarters of an hour. Afterwards, the mixture was stirred at room temperature for another 30 minutes. While the mixture was being cooled with a water bath, a solution of 18.1 grams of 2-indanone in 75 ml of THF was dosed to it in 1 hour, followed by stirring for three quarters of an hour at room temperature. Working up was as follows: the reaction mixture was poured out into water, extracted with diethylether, the ether layers were dried over magnesium sulphate, the magnesium sulphate was filtered off, the filtrate evaporated; the yield was 27.4 grams of crude reaction product. After vacuum distillation, 22.4 grams (80%) of the ethyl(2-indene)-acetate was obtained.

XIII.2. Synthesis of 2(2-indene)ethanol

A solution of 7.0 grams of ethyl(2-indene) acetate in 50 ml of diethyl ether was added in drops to a suspension of 1.41 grams of lithium aluminium hydride in 100 ml of diethyl ether, at room temperature. The temperature rose to 30° C. and the total dosing time was 60 minutes. Afterwards, the mixture was stirred for 30 minutes at room temperature. Next, 25 ml of water was added and stirring was continued for 15 minutes. The mixture was poured out into ice, and, after addition of concentrated sulphuric acid, subjected to a standard working-up procedure (vide Example I). The product was purified over a silica column (mobile phase: hexane), the yield being 4.0 grams of pure 2(2-indene)ethanol (72%).

XIII.3. Synthesis of 1-bromo-2(2-indene)ethane

To a solution of 7.1 grams of 2(2-indene)ethanol in 100 ml of THF, 11.8 grams of triphenylphosphine and subsequently, in small portions, 8.0 grams of N-bromo-succinimide were added, at room temperature. The total dosing time was 1 hour, which was followed by 30 minutes' stirring at room temperature. The reaction mixture was poured out into 300 ml of hexane and the precipitate formed was filtered off and washed two times with 50 ml of hexane. The combined hexane fractions were evaporated and the product was purified over a silica column (mobile phase: hexane). Yield: 7.9 grams of 1-bromo-2(2-indene) ethane (80%).

XIII.4 Synthesis of 1-cyclopentadiene-2(2-indene)ethane

To a solution of 120 mmol of cyclopentadiene sodium (NaCp) in 260 ml of THF, a solution of 18.2 grams of 1-bromo-2(2-indene)ethane in 100 ml of THF was added in two hours at −35° C., after which the mixture was stirred for another 30 minutes at this low temperature and subsequently for 16 hours at room temperature. After addition of water, evaporation of THF, extraction with diethyl ether, drying of the organic layers and evaporation of the solvent, the product was purified over silica (mobile phase: petroleumether 40-60). Yield: 7.1 grams (41%) of 1-cyclopentadiene-2(2-indene)ethane.

XIII.5 Synthesis of (1-cyclopentadienyl-2(2-indenyl)ethane) zirconium chloride

As in Example I.2, this time with:

2.94 grams of 1-cyclopentadiene-2(2-indene)ethane, 17.6 ml of n-BuLi, 3.2 grams of zirconium tetrachloride.

5.05 grams of solid pale-yellow compound as in the title were obtained. A portion of this product was made free of lithium chloride by extraction with dichloromethane.

Example XIV

XIV.1. Synthesis of 2-hydroxymethylene-1-indanone

To a solution of 15.5 grams of sodium ethoxide in 150 ml of t-butyl-methyl-ether, a solution of 26.7 grams of 1-indanone and 16.2 grams of ethyl formiate in 250 ml of of t-butyl-methyl-ether was added in 1 hour while cooling with a water/ice bath. Afterwards, the reaction mixture was stirred for one-and-a-half hours at room temperature. A solution of 13.7 grams of acetic acid in 100 ml of water was added. After working up of the organic layer, 27.7 grams of product (85%) was obtained.

XIV.2. Synthesis of 2-(1-keto-2-indene-methylene)-indan-1-one

After 23.1 grams of 2-hydroxymethylene-1-indanone had been heated to 120° C. for three quarters of an hour, 220 ml of m-xylene were added. After one quarter of an hour the mixture was cooled and the product crystallized. Yield: 11.6 grams (60%).

XIV.3. Synthesis of bis-2-indanone-1-methane

An amount of 5 grams of finely ground product obtained in step XIV.2, together with 90 ml of ethylacetate and 1 gram of Raney nickel, was reacted with hydrogen for three-and-a-half hours in an autoclave at 25° C. and 0,54 MPa. The reaction mixture was then filtered off and the filtrate was evaporated to 50%. Addition of hexane and cooling yielded a white crystalline compound. By repeating the crystallization three times, 3.5 grams (70%) of product was ultimately obtained.

XIV.4. Synthesis of bis-2-indenemethane

At 58° C., 3.99 grams of the diketone of step XIV.3, together with 2 drops of concentrated hydrochloric acid, were added to a solution of 5.95 grams of toluene-4-sulphonhydrazide in 40 ml of 96% ethanol. This reaction mixture was refluxed for 10 minutes. After cooling in a water/ice bath, the product (bis-hydrazone) was filtered off, dried and ground (7.68 grams, 87%).

To 10.24 grams of diisopropylamine and 50 ml of tetramethylethylenediamine, 40 ml of 1.6 M MeLi in ether was added for 15 minutes at 0° C. Five minutes later, 5 grams of the bis-hydrazone was added in 4 minutes, after which the mixture was heated to room temperature. This mixture was stirred for 17 hours. Working up (adding water, working up organic layers) yielded a crude reaction product, which was purified by crystallization from hexane. Yield: 0.47 gram of bis-2-indenemethane.

XIV.5. Synthesis of (bis-(2-indenyl)methane) zirconium dichloride

As in Example I.2, this time with:

0.40 gram bis-(2-indene)methane, 2.0 ml of n-BuLi, 0.40 gram zirconium tetrachloride.

0.56 gram of a solid, orange compound, (bis-(2-indenyl)methane) zirconium dichloride, was obtained.

Example XV

Ethylene Polymerisation

Ethylene was polymerised under conditions as described in Example IV. This time, however, the catalyst of Example XI was used, in the form of 1 ml of a 0.015 M suspension in gasoline. This catalyst was premixed with 10 ml of a 1.6 M MAO/toluene solution (Schering) for 1 minute before the mixture was added to the reactor at a reactor temperature of 155° C. The polymerisation was stopped after 7 minutes. Yield: 42.5 grams of polyethylene.

Example XVI

Ethylene Polymerisation

Polymerisation as described in Example XV, but this time with using 1 ml of a 0.010 M suspension of the catalyst of Example XIII and 6.7 ml of a 1.6 M MAO/toluene solution (Schering). Yield: 34 grams of polyethylene.

Example XVII

Ethylene Polymerisation

Polymerisation as described in Example XV, but this time with using 1 ml of a 0.015 M suspension of the catalyst of Example XIV and 10 ml of a 1.6 M MAO/toluene solution (Schering). Yield: 29 grams of polyethylene.

Comparative Experiment H

Ethylene Polymerisation

Polymerisation as described in Example XV, but this time with 1 ml of a 0.015 M suspension of $Cp_2ZrCl_2$ and 10 ml of a 1.6 M MAO/toluene solution (Schering). Yield: 11.5 grams of polyethylene.

Comparative Experiment J

Ethylene Polymerisation

Polymerisation as described in Example XV, but this time with 1 ml of a 0.015 M suspension of $(1-Ind)_2ZrCl_2$ and 10 ml of a 1.6 M MAO/toluene solution (Schering). Yield: 14.5 grams of polyethylene.

Example XVIII

Ethylene/Propylene Polymerisation

The reaction product of example XI was used for the solution copolymerisation of ethylene and propylene as described in Example VI. The Zr concentration in the reactor was 8 μmol/l; the feed temperature was 40° C. This time the Al/Zr ratio was 1250. After 30 minutes' polymerisation, during which a maximum reaction temperature of 50° C. occurred, 35 grams of clear rubber without visible homopolymer by-product was isolated and worked up. The $C_3$ content was 53 wt. %; the intrinsic viscosity was 0.1 dl/g.

Example XIX

Ethylene/Propylene Polymerisation

The reaction product of example XII was used for the solution copolymerisation of ethylene and propylene as described in Example VI. This time 6 μmol Zr/l was used and the Al/Zr ratio was 1670. The propylene/ethylene ratio in the gas phase was 6; the feed temperature 40° C. After 30 minutes' polymerisation, during which a maximum reaction temperature of 46° C. occurred, 26 grams of clear rubber without visible homopolymer by-product was isolated and worked up. The $C_3$ content of the product thus obtained was 62 wt. %; the intrinsic viscosity was 0.1 dl/g.

The products of Examples XVIII and XIX both had <2% $C_3$-inversions in the polymer chain.

Comparative Experiment K
Ethylene/Propylene Polymerisation $Me_2Si(3\text{-}Me\text{-}Cp)_2ZrCl_2$ was used for the solution copolymerisation of ethylene and propylene as described in Example VI. The Al/Zr ratio was 2500. After 30 minutes' polymerisation, 5.2 grams of low-molecular-weight inhomogeneous product was isolated and worked up.

Comparative Experiment L
Ethylene/Propylene Polymerisation

In this experiment $VOCl_3$ was used as catalyst, in a concentration of 12.5 μmol/l. As cocatalyst, sesquiethyl aluminium chloride was used, in such an amount that the Al/V ratio was 16. As promoter, dichlorophenyl-acetic acid ethyl ester (DCPAE) was used, the DCPAE/V ratio being 4. A solution polymerisation of ethylene and propylene was carried out as described in Example VI. The propylene/ethylene ratio in the gas phase was 2 and the inlet temperature was 30° C. After 10 minutes' polymerisation, during which a maximum reaction temperature of 40° C. occurred, the catalyst no longer showed any activity; 9 grams of clear rubber was obtained (Hoekstra 85). The $C_3$ content of this rubber was 38 wt. %; the DSC measurement revealed a crystallization temperature of –6° C.

Example XX

XX.1. Synthesis of methyl(2-indenyl)sulphide 11.0 grams of methanethiol was added to a solution of 13.7 grams of 2-indanone in 200 ml of chloroform. Next, a solution of 17.2 grams of trimethyl-chlorosilane in 30 ml of chloroform was added in 15 minutes, after which the mixture was stirred for 20 hours at room temperature. Thereafter, 25 ml of water was added dropwise, the mixture was extracted three times with 50 ml of a 10 wt. % sodiumhydroxide in water solution. The organic layer was evaporated; to the residu 150 ml of methanol and 15 drops of concentrated sulphuric acid were added. After a heating under reflux for 20 hours, 60 ml of water and 10 ml of a saturated sodiumbicarbonate solution were added. The methanol was evaporated, the remaining residue three times extracted with ether. The ether layers were dryed over $MgSO_4$. After evaporation, the remaining residue was purified over a silica column (mobile phase: gasoline/THF=20/1). The yield was 10.98 grams (=65%).

XX.2 Synthesis of bis(methyl(2-indenyl)sulphide) zirconiumdichloride

As in Example I.2, this time with:

1.74 grams of methyl(2-indenyl)sulphide, 7.0 ml of n-BuLi solution, 1.25 grams of zirconiumtetrachloride.

After extraction with $CH_2Cl_2$, evaporation and drying 2.0 grams of a solid yellow compound, bis(methyl(2-indenyl)sulphide)zirconiumdichloride was obtained.

Example XXI

XXI.1. Synthesis of benzyl(2-indenyl)sulphide

To a solution of 2.77 grams of 2-indanone in 150 ml of chloroform, 5.40 grams of benzylthiol was added. Next, a solution of 4.27 grams of trimethylchlorosilane in 25 ml of chloroform was added in 30 minutes, after which the mixture was stirred for 90 hours at room temperature. The mixture was extracted three times with 30 ml of a 5 wt. % sodiumhydroxide in water solution, after which the organic layer was evaporated. The residu was dissolved in 150 ml of methanol and after addition of 10 drops of concentrated sulphuric acid, stirred for 2 hours under reflux. After cooling to room temperature, the crystallized product was filtered and dried. The yield was 2.91 grams (51%).

XXI.2. Synthesis of bis(benzyl(2-indenyl)sulphide) zirconiumdichloride

As in Example XX.2, this time with:

1.46 grams of benzyl(2-indenyl)sulphide, 3.8 ml n-BuLi solution, 0.72 grams of zirconiumtetrachloride.

1.1 grams of the title compound was obtained (91%).

Example XXII

XXII.1. Synthesis of n-butyl(2-indenyl)sulphide 19.3 grams of 1-butanethiol was added to a solution of 13.4 grams of 2-indanone in 200 ml of chloroform. Next, a solution of 23.5 grams of trimethylchlorosilane in 50 ml of chloroform was added in 30 minutes, after which the mixture was stirred for 65 hours at room temperature. Thereafter, 25 ml of water was added dropwise and the mixture extracted three times with 50 ml of a 5 wt. % sodiumhydroxide solution in water. The organic layer was dried over $MgSO_4$, evaporated and destilled under vacuum. The residue was dissolved in 150 ml of methanol; 15 drops of concentrated sulphuric acid were added and refluxed for 2 hours. After cooling to room temperature, 10 ml of a $NH_3$-solution was added; methanol was evaporated; 50 ml of water was added to the residu. After 3 extractions with ether, the etherlayers were dryed over $MgSO_4$ and evaporated. The yield was 10.7 grams (52%).

XXII.2. Synthesis of bis(n-butyl(2-indenyl)sulphide) zirconiumdichloride

As in Example XX.2, this time with:

4.51 grams of n-butyl(2-indenyl)sulphide, 13.8 mol n-BuLi-solution, 2.57 grams of zirconiumtetrachloride.

2.0 grams of a yellow powder of the title compound (32%) was obtained.

Example XXIII

XXIII.1. Synthesis of phenyl(2-indenyl)sulphide 17.7 grams of thiophenol was added to a solution of 10.2 grams of 2-indanon in 200 ml of chloroform. Next, a solution of 16.9 grams of trimethylchlorosilane in 50 ml of chloroform was added in 30 minutes, after which the mixture was stirred for 65 hours at roomtemperature. Thereafter, the mixture was extracted three times with 50 ml of a 5 wt. % sodiumhydroxide in water solution, after which the organic layer was evaporated. To the residue 250 ml of methanol and 25 drops of concentrated sulphuric acid was added and the mixture heated for two hours under reflux. After evaporation, the remaining residue was purified over a silica column (mobile phase: hexane/THF=20/1). The yield was 7.84 grams (45%).

XXIII.2. Synthesis of bis(phenyl(2-indenyl)sulphide) zirconiumdichloride

As in Example XX.2, this time with:

2.31 grams of phenyl(2-indenyl)sulphide, 6.4 ml n-BuLi-solution, 1.26 grams of zirconiumtetrachloride.

2.1 grams of a yellow powder of the title compound (66%) was obtained.

Examples XXIV to XXVII
Ethylene Polymerisation

In the following examples, a 1.5 l reactor was filled with 450 ml of gasoline, pressurized with ethylene and brought to reaction condition (50° C.; pressure=0.7 MPa). To the reactor was added 3.3 ml of MAO (1.6 M in toluene). 25 ml of gasoline and 0.25 ml of a 0.01 M solution of a 2-indenyl compound were mixed and added to the reactor. An after-rinse was performed with 25 ml of gasoline. After 7 minutes of polymerisation at 50° C. and 0.7 MPa, the polymerisation was stopped by releasing the pressure to atmospheric pressure and the polyethylene was isolated and dried. The respective 2-indenyl compounds used are the compounds of Examples XX to XXIII. The polymerisation results are given in the following table:

| Example | Catalyst from Example | Result* | Yield** |
|---|---|---|---|
| XXIV | XX | 10.3 | 32 |
| XXV | XXI | 57.0 | 177 |
| XXVI | XXII | 5.8 | 18 |
| XXVII | XXIII | 4.8 | 15 |

*Result: grams of polyethylene obtained
**Yield: expressed in kg polyethylene/grams transition metal .5 minutes

We claim:

1. A process for polymerizing an olefin which comprises contacting at least one olefin with a 2-indenyl compound having an unsaturated aromatic six-membered ring, in the presence of a cocatalyst, under effective polymerization conditions, wherein said 2-indenyl compound is represented by the general formula $$R'Ind\text{—}M\text{—}(CP)\text{—}Q_k \qquad (1)$$

wherein
Ind represents an indenyl group,
R' represents a substituent, other than hydrogen, bound to the Ind group at the 2-position,
Cp represents a cyclopentadienyl group,
M represents a transition metal from group 4, 5, or 6 of the Periodic System of Elements,
Q represents a ligand to M, and
k is an integer linked to the valence of M, wherein k equals the valence of M minus two divided by the valence of Q, and
wherein in said process for polymerizing an olefin, processes utilizing compounds in which the Cp-group is an indenyl group and in which either:
a) the Ind- and the Cp-groups are bridged over the respective 1-positions,
b) the indenyl compound is bis(2,3-dimethyl-1-indenyl)-zirconiumdichloride, or
c) the indenyl compound is either ethylene-1-(3-but-3-enyl) inden-1-yl-2-((1-but-3-enyl)-inden-2-yl)-zirconiumdichloride, or ethylene-1-((3-allyldimethylsilyl) inden-1-yl)-2-((1-allyldimethylsilyl)inden-2-yl)zirconium-dichloride, are disclaimed as the process for polymerizing an olefin with a 2-indenyl compound.

2. A process according to claim 1, wherein R' is an alkyl group.

3. A process according to claim 1 wherein the Cp group is a 2-indenyl group represented by the formula:

R"Ind wherein R" represents a substituent other than hydrogen at the 2-position of the Ind group.

4. A process according to claim 3, wherein R" is an alkyl group.

5. A process according to claim 4, wherein said alkyl group contains 1–4 carbon atoms.

6. A process according to claim 1, wherein R' forms a bridge between the Ind group and the Cp group in formula (1).

7. A process according to claim 6, wherein said indenyl compound is represented by the formula:

wherein R is bound at the 2-position to both 2-Ind groups, wherein R is a hydrocarbon group or a group with at least one heteroatom from group 14, 15 or 16 of the Periodic System of Elements.

8. A process according to claim 7, wherein R is selected from the group consisting of a methylidene group, an ethylidene group and a group having at least one heteroatom from group 14, 15 or 16 of the Periodic System of Elements.

9. A process according to claim 8, wherein R contains a heteroatom selected from the group consisting of silicon, nitrogen, phosphorus, oxygen and sulphur.

10. A process according to claim 8, wherein said R-group is a sulphur atom, —(CH$_2$)$_2$—S—(CH$_2$)$_2$—, an oxygen atom, (CH$_3$)$_2$Si=, —Si(CH$_3$)$_2$—Si(CH$_3$)$_2$—, Ge(CH$_3$)$_2$—, (phenyl)P=, or (phenyl)N=.

11. A process according to claim 8, wherein said R group is a hydrocarbon group.

12. A process according to claim 1, wherein said at least one olefin is selected from the group consisting of ethylene, α-olefin, internal olefin, and diolefin.

13. A process according to claim 1, wherein said at least one olefin is selected from the group consisting of ethylene, propylene, butene, pentene, heptene, and octene.

14. A process according to claim 1, wherein said polymerization yields a polymer based on at least one of olefin selected from the group consisting ethylene and propylene.

15. A process according to claim 13, wherein said polymerization yields a rubbery polymer based on ethylene, propylene and, optionally, a diene.

16. A process for polymerizing at least one olefin which comprises contacting at least one olefin with a 2,2'-bridged bisindenyl Group 4, 5, or 6 metallocene compound, in the presence of a cocatalyst, under effective polymerization conditions.

17. A process for polymerizing at least one olefin which comprises contacting at least one olefin with a 2,2'-bridged bisindenyl Group 3 or lanthanide metallocene compound under effective polymerization conditions.

18. A process for polymerizing an olefin which comprises contacting at least one olefin with a 2-indenyl compound, optionally in the presence of a cocatalyst, under effective polymerization conditions, wherein said 2-indenyl compound is represented by the general formula $$R'Ind\text{—}M\text{—}(Cp)\text{—}Q_k \qquad (1)$$

wherein
Ind represents an indenyl group,
R' represents a substituent, other than hydrogen, bound to the Ind group at the 2-position,
Cp represents a cyclopentadienyl group,
M represents a transition metal from group 3 and the lanthanides of the
Periodic System of Elements,
Q represents a ligand to M, and
k is an integer linked to the valence of M, wherein k equals the valence of M minus two divided by the valence of Q.

* * * * *